United States Patent [19]

Nakamura et al.

[11] Patent Number: 4,996,236
[45] Date of Patent: Feb. 26, 1991

[54] THERAPEUTIC COMPOSITION FOR HEPATIC ENCEPHALOPATHY

[75] Inventors: Nobuto Nakamura; Hiroshi Satoh, both of Osaka; Matsuo, Kyoto, all of Japan; Misael U. Esquivel, Tlalpan, Mexico

[73] Assignee: Takeda Chemical Industries, Ltd., Osaka, Japan

[21] Appl. No.: 351,462

[22] Filed: May 15, 1989

[30] Foreign Application Priority Data

Jun. 22, 1988 [JP] Japan .................. 63-153845

[51] Int. Cl.$^5$ .................. A61K 31/13; A61K 31/44; A61K 31/38
[52] U.S. Cl. .................. 514/659; 514/352; 514/438; 514/660
[58] Field of Search .................. 514/23, 438, 53, 277, 514/461, 659, 352, 660; 564/362

[56] References Cited

PUBLICATIONS

Therapeiwoche, vol. 34, No. 17, 1984, G. Braun Lerlag Zeitschriften, Karlsruhe, DE: D. Müting: "Acarbose bei der Behandlung von Diabetiken mit Gleichzeitiger Leberzirrhose", pp. 2566-2572.
Drugs of the Future, vol. 11, No. 9, 1986, pp. 729-731.
J. Med. Chem., No. 29, 1986, American Chemical Society; S. Horii et al.: "Synthesis and Alpha-D-Glucosidase Inhibitory Activity of N-substituted Valioalmine Derivatives as Potential Oral Antidiabetic Agents", pp. 1038-1046.
Jpn. J. Gastroenterologie, vol. 84, No. 8, 1987, pp. 1639-1644.
The Journal of Antibiotics, vol. 37, No. 11, Nov. 1984, Y. Kameda et al.: "Valiolamine, a New Alpha-Flucosidase Inhibiting Aminocyclitol Produced by *Streptomyces hygroscopicus*", pp. 1301-1307.
Chem Abst, 108:68718u, (1988), Yoshiaki et al.
Chem Abst, 104:207548w, (1986), Satoshi et al.
Dtsch. Med. Worchenschr. 108, No. 4, 157 (1983).

Primary Examiner—Stanley J. Friedman
Assistant Examiner—Zohreh A. Fay
Attorney, Agent, or Firm—Wegner, Cantor, Mueller & Player

[57] ABSTRACT

A pharmaceutical composition for the treatment of hyperammonemia which comprises a valiolamine compound of the formula

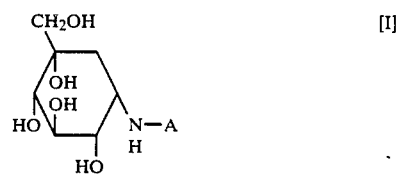

wherein A means an acyclic hydrocarbon group of 1 to 10 carbon atoms which may optionally be substituted by hydroxy, phenoxy, thienyl, furyl, pyridyl, chclohexyl or optionally substituted phenyl; a 5- or 6-membered cyclic hydrocarbon group which may optionally be substituted by hydroxy, hydroxymethyl, methyl or amino; or a saccharide residue or a pharmaceutically acceptable salt thereof, the use of said valiolamine compound of the formula [I]0 or a pharmaceutically acceptable salt thereof in the preparation of a medicine for the treatment of hyperammonemia, and a method for the treatment of hyperammonemia which comprises administrating a valiolamine compound of the formula [I] or a pharmaceutically acceptable salt thereof.

2 Claims, No Drawings

THERAPEUTIC COMPOSITION FOR HEPATIC ENCEPHALOPATHY

This invention relates to a therapeutic composition for hyperammonemia which comprises an N-substituted valiolamine derivative and its use.

Hyperammonemia is frequently found in patients with serious liver diseases such as fulminant hepatitis, subacute hepatitis and terminal stage liver cirrhosis. The psychoneurological syndrome observed in those patients with liver disease is known as hepatic encephalopathy and it is generally acknowledged that an elevated blood ammonia level is closely associated with its pathophysiology. Therefore, the management of hyperammonemia constitutes a cardinal part of therapeutics for hepatic encephalopathy.

The major part of blood ammonia is contributed by the ammonia produced on decomposition of dietary protein by intestinal bacteria. Therefore, for the relief of hepatic encephalopathy, certain synthetic disaccharides (for example, lactulose) which are conducive to a decreased ammonia output in the intestines are generally utilized. It is recognized that synthetic disaccharides not only act as laxatives due to their osmotic pressure effect to promote evacuation of the bowels but their decomposition products depress the intestinal pH to inhibit growth of ammonia-producing microorganisms and, at the same time, inhibit absorption of ammonia.

On the other hand, it has been reported that acarbose, an α-glucosidase inhibitor, lowers the blood ammonia level in diabetics accompanied with hepatocirrhosis [Dtsch. Med. Wochenschr. 108, No. 4,157 (1983) and Therapiewoche 34, No. 17, 2566, 2570–2572 (1984)]. However, there has not been available an established therapeutic modality for hyperammonemia, particularly for hepatic encephalopathy.

The inventors of this invention, paying attention to the α-glucosidase-inhibitory activity of N-substituted valiolamine derivatives, explored their various pharmacological actions and found that these derivatives at low doses produced marked decreases in blood ammonia.

Thus, this invention is directed to a therapeutic composition for hyperammonemia which comprises a valiolamine compound of the formula

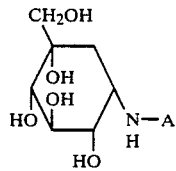

[I]

wherein A means an acyclic hydrocarbon group of 1 to 10 carbon atoms which may optionally be substituted by hydroxy, phenoxy, thienyl, furyl, pyridyl, cyclohexyl or optionally substituted phenyl; a 5- or 6-membered cyclic hydrocarbon group which may optionally be substituted by hydroxy, hydroxymethyl, methyl or amino group; or a saccharide residue.

The valiolamine compound [I] to be used in this invention is a known compound and its description and the technology for production thereof have been disclosed in Japanese Patent Application KOKAI No. 200335/1982 (corresponding to U.S. Pat. No. 4701559) and KOKAI No. 59946/1983 (corresponding to U.S. Pat. No. 4701559). Specifically referring to the compounds [I], the acyclic hydrocarbon group of 1 to 10 carbon atoms represented by A includes straight-chain saturated aliphatichydrocarbon groups such as ($C_{1-10}$) alkyl e.g. methyl, ethyl, propyl, butyl, pentyl, hexyl, heptyl, octyl, nonyl and decyl; branched saturated aliphatic hydrocarbon groups, such as lower ($C_{3-5}$) alkyl e.g. isopropyl, isobutyl, sec-butyl, tert-butyl, neopentyl and tert-pentyl, ($C_{4-9}$) alkyl having one or two methyls e.g. 1-methylbutyl, 2-methylbutyl, isohexyl, 1-methylpentyl, 2-methylpentyl, 3-methylpentyl, 4-methylpentyl, methylhexyl exemplified by 5-methylhexyl, etc., methylheptyl exemplified by 1-methylheptyl, etc., methyloctyl, methylnonyl, 1-methylisobutyl, 1-methylisopentyl, dimethylbutyl exemplified by 1,1-dimethylbutyl, etc., dimethylpentyl exemplified by 1,1-dimethylpentyl, 1,4-dimethylpentyl, etc., dimethylhexyl, dimethylheptyl and dimethyloctyl, ($C_{3-8}$) alkyl having one to two ethyls e.g. 1-ethylpropyl, ethylbutyl, ethylpentyl, ethylhexyl, ethylheptyl and ethyloctyl, ($C_{3-4}$) alkyls having methyl and ethyl e.g. ethylmethylpropyl exemplified by 1-ethyl-1-methylpropyl, etc., ethylmethylbutyl exemplified by 1-ethyl-2-methylbutyl, 1-ethyl-3-methylbutyl, etc., and propylbutyl exemplified by 1-isopropylbutyl, etc.; and straight-chain and branched unsaturated aliphatic hydrocarbon groups such as propenyl exemplified by vinyl, allyl, etc., butenyl exemplified by 3-butenyl, etc., pentenyl exemplified by 4-pentenyl, etc., hexenhl, heptenyl, octenyl, nonenyl, decenyl, butadienyl, pentadienyl, hexadienyl, heptadienyl, octadienyl, nonadienyl, decadienyl, hexatrienyl, heptatrienyl, octatrienyl, nonatrienyl, decatrienyl, octatetraenyl, nonatetraenyl, decatetraenyl, decapentaenyl, isopropenyl, methylpropenyl exemplified by 2-methylallyl, etc., dimethylpropenyl exemplified by 1,1-dimethylallyl, etc., methylbutenyl exemplified by 3-methyl-2-butenyl, 3-methyl-3-butenyl, etc., and dimethyldienyl unsaturated hydrocarbon groups exemplified by 3,7-dimethyl-2,6-octadienyl, etc. As preferable ones among them, there may be mentioned acyclic hydrocarbons of 1 to 6 carbon atoms. These hydrocarbon groups may be substituted by one or more; preferably one to six, of hydroxy, cyclohexyl, phenoxy, thienyl, furyl, pyridyl or a phenyl group which may be substituted with hydroxy, a lower alkoxy such as methoxy, ethoxy, n-propoxy and isopropoxy carboxyl, a halogen such as fluorine, chlorine, bromine and iodine, phenyl or a lower alkyl such as methyl, ethyl, propyl, isopropyl, butyl, sec-butyl and tert-butyl. Preferably the above-mentioned substituents are hydroxy or phenyl groups which may be substituted by hydroxy, lower alkoxy, lower alkyl or halogen. The 5- or 6-membered cyclic hydrocarbon group represented by A includes cyclic saturated hydrocarbon groups such as cyclopentyl and cyclohexyl and cyclic unsaturated hydrocarbon groups such as cyclopentenyl and cyclohexenyl. These cyclic hydrocarbon groups may be optionally substituted by one to six hydroxy, hydroxymethyl, methyl or amino groups. The saccharide residue means a group obtainable upon elimination of one hydrogen atom from a saccharide molecule, and may, for example, be a residue derived from a monosaccharide or oligosaccharide. As specific examples of compound [I], there may be mentioned N-(1,3-dihydroxy-2-propyl)valiolamine, N-phenethylvaliolamine, N-thenylvaliolamine, N-(cyclohexyl-methyl)valiolamine, etc. These compounds may be used in the form of salts with inorganic acids such as hydrochloric acid etc. or organic acids such as citric acid etc. Incidentally, it is already known that these derivatives have α-glucosidase inhibitory activity and are useful as antidiabetic and antiobesic agents.

This invention is, therefore, directed to the use of valiolamine compound [I] in the treatment of hyperammonemia and particularly hepatic encephalopathy and the use of valiolamine compound [I] in the manufacture of pharmaceutical products for the treatment of such diseases.

In this invention, the valiolamine compound [I] can be formulated with various pharmaceutically acceptable vehicles or carriers for use as therapeutic compositions. The route of administration is peroral or per-rectal. Accordingly, the therapeutic compositions of this invention can be administered as solid oral preparations, such as tablets, capsules, etc., or as suppositories.

In the manufacture of solid oral preparations such as tablets, various additives such as binders (e.g. starch, hydroxypropylcellulose, hydroxypropylmethylcellulose, Macrogol, etc.), disintegrating agents (e.g. starch, carboxymethylcellulose calcium, low-substituted hydroxypropylcellulose, etc.), excipients (e.g. lactose, starch, etc.) and/or lubricating agents (e.g. magnesium stearate, talc, etc.) can be added in appropriate amounts. For the manufacture of suppositories, lipophilic bases such as cacao butter, Witepsol, etc. or hydrophilic bases such as polyethylene glycol, glycerogelatin, etc. can be selectively employed in appropriate amounts.

In the pharmaceutical compositions of the present invention, including the above-mentioned solid preparations, the valiolamine compound [I] is contained appropriately in an effective hyperammonemia-reducing amount.

The valiolamine compound [I] is generally contained in the pharmaceutical compositions in a proportion in the range from 0.0001 parts by weight to 100 parts by weight relative to the total composition.

The pharmaceutical compositions used in the present invention such as solid preparations such as tablets, capsules, etc., or suppositories can be manufactured, if necessary or suitable, with the use of said additives in accordance with a conventional pharmaceutical procedure e.g. by mixing the ingredients.

The dosage of valiolamine derivative depends on the route of administration, clinical condition, etc. Usually, however, in adults, this drug is used generally in the dose of 0.01 to 100 mg/day or preferably in the dose of 0.1 to 10 mg/day, most preferably 0.1 to 5 mg/day, generally in 2 or 3 divided doses daily and preferably before each meal.

The valiolamine derivative to be used in this invention, for example, N-(1,3-dihydroxy-2-propyl)valiolamine, is a highly safe compound and its acute oral $LD_{50}$ values in mice (NRMI) and rats (Wistar) are 14.7-21.5 g/kg (mice) and about 20 g/kg (rats).

Thus, the pharmaceutical composition comprising a valiolamine compound of the formula [I] as the active ingredient used in this invention causes lowering of the blood ammonia level in mammalian animals in small doses and is of great use as a prophylactic and therapeutic agent for various diseases associated with hyperammonemia, for example, hepatic encephalopathy.

The following test and working examples are further illustrative of this invention.

TEST EXAMPLE 1

The blood ammonia level-lowering effect of N-(1,3-dihydroxy-2-propyl)valiolamine in rats Male SD rats aged 67 weeks were fed either on a regular diet or a high-protein powder diet containing 61% of casein for 7 days. N-(1,3-dihydroxy-2-propyl)-valiolamine (hereinafter referred to shortly as AO-128) was added to the high-protein diet at final concentrations of 10 and 50 ppm. The animals had free access to the diets and the mean daily food intake was approximately 18 g/day. On the 7th day, laparotomy was performed under ether anesthesia and the blood was collected from the abdominal aorta. The blood ammonia level was estimated using an assay kit, a product of WAKO. The results are set forth in Table 1.

It is apparent from Table 1 that the high-protein diet control group showed a higher blood concentration of ammonia than the regular diet control group but the AO-128 treated high-protein diet group showed an overtly lower blood ammonia level than the high-protein diet control group, indicating clearly that AO-128 has the activity to lower the blood ammonia level.

TABLE 1

| Group | Number of animals | Blood ammonia level ($\mu$g/dl) |
| --- | --- | --- |
| Regular diet control group | 5 | 103 ± 2 |
| High-protein diet control group | 5 | 127 ± 23 |
| AO-128 (10 ppm)-treated high-protein diet group | 5 | 88 ± 7 |
| AO-128 (50 ppm)-treated high-protein diet group | 5 | 90 ± 8 |

Note
Each concentration value is the mean ± S.D.

EXAMPLE 1

According to the following formula, tablets for oral administration are manufactured by the below-mentioned pharmaceutical procedure.

| | |
| --- | --- |
| N-(1,3-Dihydroxy-2-propyl)valiolamine | 0.05 mg |
| Corn starch | 30 mg |
| Lactose | 76.65 mg |
| Hydroxypropylcellulose | 3.0 mg |
| Magnesium stearate | 0.3 mg |
| Total | 110.0 mg |

N-(1,3-Dihydroxy-2-propyl)valiolamine, corn starch and lactose are fully mixed. The mixture is kneaded with an aqueous solution of hydroxypropylcellulose. The kneaded mixture is dried and comminuted, followed by the addition of magnesium stearate. The mixture is further mixed and compressed into tablets.

EXAMPLE 2

N-(1,3-Dihydroxy-2-propyl)valiolamine (0.1 mg) and Witepsol W-35 (1999.9 mg) are throughly mixed at 70°-80° C. to give a homogeneous mixture. The mold for suppositories is charged with the obtained mixture for molding, followed by cooling to room temperature to give suppositories for rectal administration.

We claim:

1. A method for the treatment of hyperammonemia which comprises administering to a subject in need thereof an effective hyperammonemia-reducing amount of a valiolamine compound of the formula

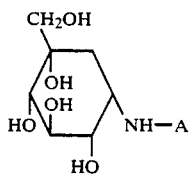

wherein A means an acyclic hydrocarbon group of 1 to 10 carbon atoms which may optionally be substituted by hydroxy, phenoxy, thienyl, furyl, pyridyl, cyclohexyl or optionally substituted phenyl; a 5- or 6-membered cyclic hydrocarbon group which may optionally be substituted by hydroxy, hydroxymethyl, methyl, or amino; or a saccharide residue or a pharmaceutically acceptable salt thereof.

2. A method for the treatment of hyperammonemia as claimed in claim 1 wherein the valiolamine compound is N-(1,3-dihydroxy-2-propyl)valiolamine.

* * * * *